United States Patent
Pawlowicz et al.

(10) Patent No.: US 9,915,628 B2
(45) Date of Patent: *Mar. 13, 2018

(54) CIRCUIT TRACING USING A FOCUSED ION BEAM

(71) Applicant: TECHINSIGHTS INC., Ottawa, Ontario (CA)

(72) Inventors: Christopher Pawlowicz, Ottawa (CA); Alexander Sorkin, Nepean (CA); Michael W. Phaneuf, Ottawa (CA); Alexander Krechmer, Ottawa (CA); Ken G. Lagarec, Ottawa (CA)

(73) Assignee: TECHINSIGHTS INC., Kanata, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/174,260

(22) Filed: Jun. 6, 2016

(65) Prior Publication Data

US 2016/0282287 A1 Sep. 29, 2016

Related U.S. Application Data

(63) Continuation of application No. 14/309,674, filed on Jun. 19, 2014, now Pat. No. 9,383,327, which is a (Continued)

(51) Int. Cl.
| | |
|---|---|
| *G21G 5/00* | (2006.01) |
| *G01N 23/225* | (2018.01) |
| *H01J 37/22* | (2006.01) |
| *H01L 21/66* | (2006.01) |
| *G01R 31/303* | (2006.01) |

(52) U.S. Cl.
CPC ........ *G01N 23/2255* (2013.01); *H01J 37/222* (2013.01); *H01L 22/12* (2013.01); *G01R 31/303* (2013.01); *H01J 2237/24564* (2013.01); *H01J 2237/24585* (2013.01);
(Continued)

(58) Field of Classification Search
CPC ............ H01J 2237/28; H01J 2237/244; H01J 2237/2516; H01J 2237/2806; H01J 37/26; H01J 37/3006; G01N 23/2251; G01N 27/60; G01R 31/307
USPC .......... 250/306, 307, 309, 311, 492.1, 492.2, 250/492.21, 492.3
See application file for complete search history.

(56) References Cited

U.S. PATENT DOCUMENTS

| 8,791,436 B1 | 7/2014 | Pawlowicz et al. |
| 2008/0237487 A1 | 10/2008 | Pinto et al. |
| 2010/0038555 A1 | 2/2010 | Tsao |

*Primary Examiner* — Wyatt Stoffa
*Assistant Examiner* — Hanway Chang
(74) *Attorney, Agent, or Firm* — Knobbe, Martens, Olson & Bear, LLP (57) ABSTRACT

Methods and systems for tracing circuitry on integrated circuits using focused ion beam based imaging techniques. A first component or node on an integrated circuit is coupled to a second component or node on the same integrated circuit. After an external bias is applied to the first component or node, a focused ion beam is applied to the integrated circuit and an image is taken using an electron detector. The features or components on the integrated circuit which are coupled to the second component or node will show up in high contrast on the resulting image. The method may also involve applying a bias to a node or component and then using focused ion beam imaging techniques (through an electron detector) to arrive at an image of the integrated circuit. Components coupled to the node will appear in high contrast in the resulting image.

19 Claims, 5 Drawing Sheets

Related U.S. Application Data continuation of application No. 13/869,749, filed on Apr. 24, 2013, now Pat. No. 8,791,436.

(52) U.S. Cl.
CPC ............... *H01J 2237/2803* (2013.01); *H01J 2237/2809* (2013.01); *H01J 2237/31749* (2013.01)

CIRCUIT TRACING USING A FOCUSED ION BEAM

TECHNICAL FIELD

The present invention relates to circuit tracing. More specifically, the present invention relates to methods and systems for use in tracing circuit connections on an integrated circuit using a focused ion beam to capture an image of the circuit.

BACKGROUND OF THE INVENTION

The technological revolution of the late 20th and early 21st century has put a premium on competitive corporate intelligence. Companies, especially those involved in high tech, seek to determine what their competitors are putting in their latest products. To this end, integrated circuits, especially high value, cutting edge microchips, are constantly being reverse engineered, analyzed, and dissected to determine what are their internal structures and interconnections.

Currently, the dissection and analysis of integrated circuits involves a painstaking, laborious process. Each layer in a multi-layer microchip is carefully exposed and imaged/photographed. A mosaic of the images is then created and the traces are then laboriously traced to determine which feature is interconnected with which component. As can be imagined, this resource-intensive process can lead to mistakes as features and areas which may not be of interest may need to be imaged and analyzed, simply to ensure that the features of interest are covered.

There is therefore a need for systems, methods, and devices which can reduce the effort required to trace circuits and interconnects on integrated circuits.

SUMMARY OF INVENTION

The present invention provides methods and systems for tracing circuitry on integrated circuits using focused ion beam based imaging techniques. A first component or node on an integrated circuit is coupled to a second component or node on the same integrated circuit. An external bias is then applied to the first component or node. A focused ion beam is applied to the integrated circuit and an image is taken using an electron detector. The features or components on the integrated circuit which are coupled to the second component or node will show up in high contrast on the resulting image. The method can be used in an iterative process to identify which components are coupled to which features on the integrated circuit. The method may also involve applying a bias to a node or component and then using focused ion beam imaging techniques (through an electron detector) to arrive at an image of the integrated circuit. Other components or nodes coupled to the node or component to which the bias was applied will appear in high contrast on the resulting image.

In a first aspect, the present invention provides a method for imaging circuitry on an integrated circuit, the method comprising:
  a) coupling a first part of said integrated circuit with a second part of said integrated circuit;
  b) applying a bias voltage to said first part;
  c) exposing said integrated circuit to a focused ion beam; and
  d) gathering an image of said integrated circuit using an electron detector;
  wherein said first part and said second part are not coupled through said integrated circuit; and
  wherein said image gathered in step d) has at least one portion in high contrast compared to a rest of said image, said at least one portion being a portion of said integrated circuit which is coupled to said second part of said integrated circuit.

In a second aspect, the present invention provides a method for tracing interconnections in an integrated circuit, the method comprising:
  a) removing layers of said integrated circuit to expose components of said integrated circuit;
  b) coupling a first node of said integrated circuit to a second node of said integrated circuit;
  c) applying an external bias voltage to said first node;
  d) capturing an image of at least a portion of said integrated circuit using a focused ion beam and an electron detector;
  e) determining which components of said integrated circuit are illustrated in high contrast in said image;
  wherein, prior to step b), said first node and second node are not coupled to one another through said integrated circuit.

In a third aspect, the present invention provides a method for imaging circuitry on an integrated circuit, the method comprising:
  a) applying an external electrical bias on to a first portion of said integrated circuit;
  b) exposing said integrated circuit to a focused ion beam;
  c) gathering an image of said integrated circuit;
  wherein said image gathered in step c) shows a second portion of said integrated circuit which is in high contrast compared to a rest of said image, said first and second portions being interconnected through a common path in said integrated circuit.

BRIEF DESCRIPTION OF THE DRAWINGS

The embodiments of the present invention will now be described by reference to the following figures, in which identical reference numerals in different figures indicate identical elements and in which.

DETAILED DESCRIPTION OF THE INVENTION

Focused Ion Beam (FIB) systems are well established in the semiconductor industry and come in a variety of configurations for a number of different uses. In FIB systems, a focused beam is generated and the beam is accelerated down a column. The beam is then manipulated by applying electromagnetic energy through a system of coils (and electrostatic lenses), and the resulting beam emerges in a vacuum chamber and strikes a sample/target. For FIB, the beam consists of ions as ion beams have much more kinetic energy than electron beams. By striking a sample with high power, material can be milled away and removed. By adding background gas and striking the sample with lower energy, new material can be deposited. By manipulating the beam and adding a gas, one can deposit and remove material in a precise and controlled manner. Standard gases which may be used include xenon difluoride, tetramethylcyclotetrasiloxane (TMCTS), platinum, tungsten, and other well-known gases.

After the ion beam strikes a sample, ions, atoms and electrons are emitted (mostly 'secondary electrons'). These electrons can be used to create an image—an image can be obtained by using an electron detector and synchronizing the collected signal with the ion beam scanning. Depending on the sample's materials and other factors, more or less electrons might be emitted. The image can therefore be used to identify regions of the sample with different characteristics. As an example, metal circuitry will emit a different number of electrons than dielectric areas and this causes metal circuitry to appear different than dielectric areas in the image.

Figure 1:
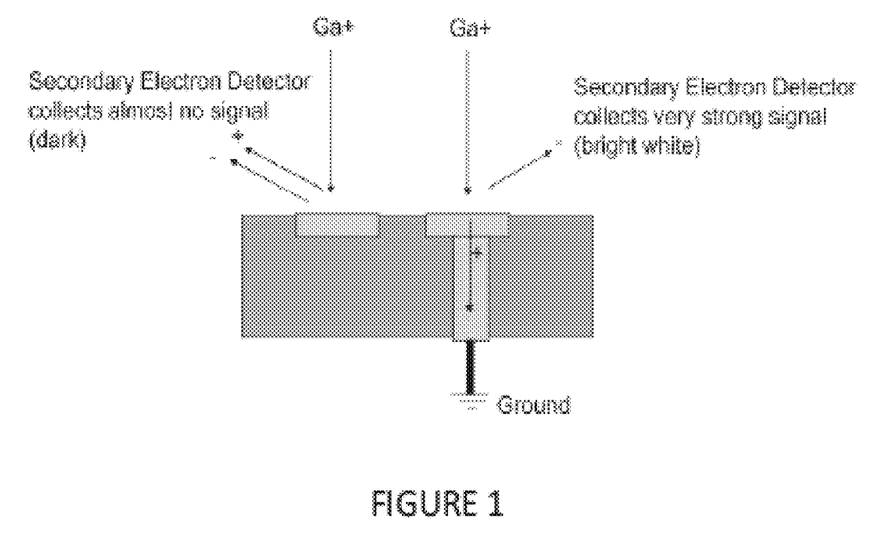
FIGS. 1 and 2 are schematic diagrams provided to explain focused ion beam (FIB) technology.

Referring to FIG. 1, a schematic view explaining focused ion beam technology is illustrated. As can be seen in FIG. 1, a focused ion beam (from a gallium ion source) is applied to a sample. The ion beam causes electrons to be emitted by the sample. These electrons are detected by a secondary electron detector. From the emitted electrons, an image of the sample can be constructed. As can also be seen in FIG. 1, by grounding one of the features of the sample and thereby rerouting positive particles, a brighter image can be obtained for the grounded feature. This is because the secondary electron detector receives a higher concentration of electrons compared to the ungrounded feature.

A well known phenomenon occurs when an ion beam strikes an area of semiconductor with embedded dopant material. Since N-doped silicon behaves differently from P-doped silicon when struck by an ion beam, the resulting image shows contrast differences between the materials. Materials other than semiconductors also show this behaviour, known as voltage contrast, in various degrees.

Figure 2:
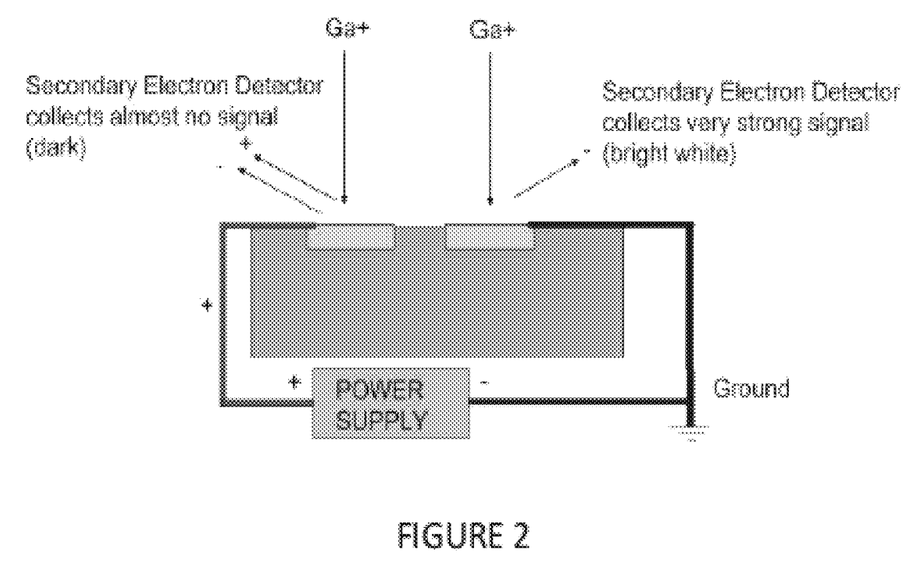

By way of explanation, FIG. 2 is provided. In this FIG., two features on an integrated circuit (IC) are coupled by means of an electrical circuit. When a focused ion beam is applied to the features, the feature on the IC which is coupled to ground produces a brighter image. Again, this is because the secondary electron detector receives a higher concentration of electrons from the grounded feature as compared to the ungrounded feature.

Figure 3:
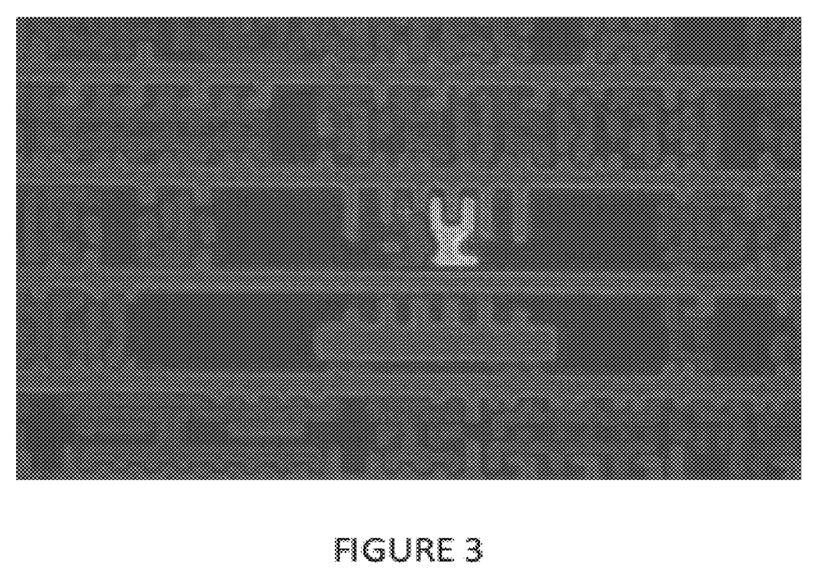
FIG. 3 is an image derived from FIB illustrating a feature of an IC in high contrast.

Extending the concept explained by FIG. 2, a focused ion beam can be used to strike a sample which has a mixture of dielectric material and metal interconnect (e.g. a delayered IC die). By making external connections to specific areas of circuitry and applying a bias voltage to those areas, the amount of electrons generated when these areas are struck by an ion beam can be made to vary greatly. Using this technique, specific areas of the integrated circuit can be made to show much higher brightness (i.e. higher contrast) in the resulting image as compared to other areas when plotting the secondary electron yield. One example of this is shown in FIG. 3 where an IC feature/component has been biased and an FIB has been applied. As can be seen, the feature to which a bias has been applied is in high contrast to the rest of the IC.

The high brightness (or high contrast) area can be extended by using normal circuit-edit FIB manipulation. By depositing dielectric material, milling access holes, and depositing metal interconnect, the biased area can be connected to a new area or a new component or node of the IC. Any areas, components, or nodes coupled to the biased area will, when struck by a focused ion beam, similarly appear in high contrast in the resulting image derived from the secondary electron detector output. This can be used to determine which features, nodes, or components on an IC are connected to which areas, features, nodes, or components.

Figure 3A:
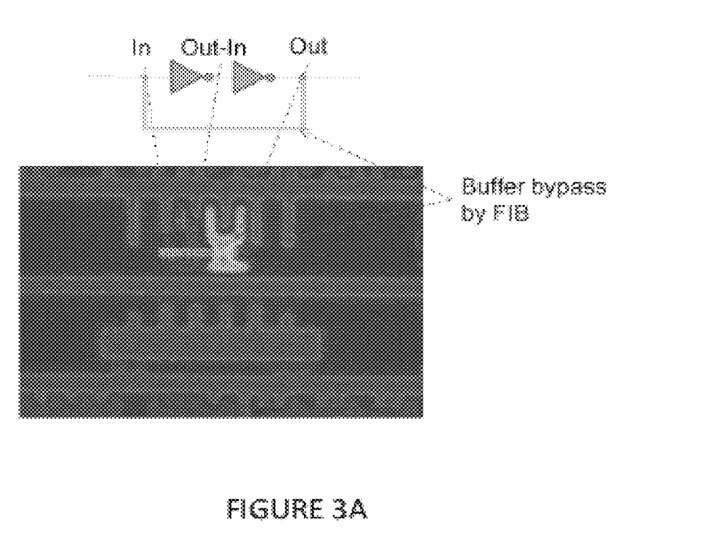
FIG. 3A is a schematic diagram with an image from FIB showing the coupling between two features on an IC.

Referring to FIGS. 3A-6, the steps in the coupling between a known feature and an unknown area or feature in the IC is illustrated. FIG. 3A shows, in a schematic diagram, the desired end result for shorting two features on the IC. As can be seen, a known feature (the buffer feature in high contrast) is to be shorted with an adjacent feature, also a buffer. The yellow block between the highlighted buffer component and its adjacent buffer represents a short that couples these buffers to one another in FIG. 3A.

Figure 4:
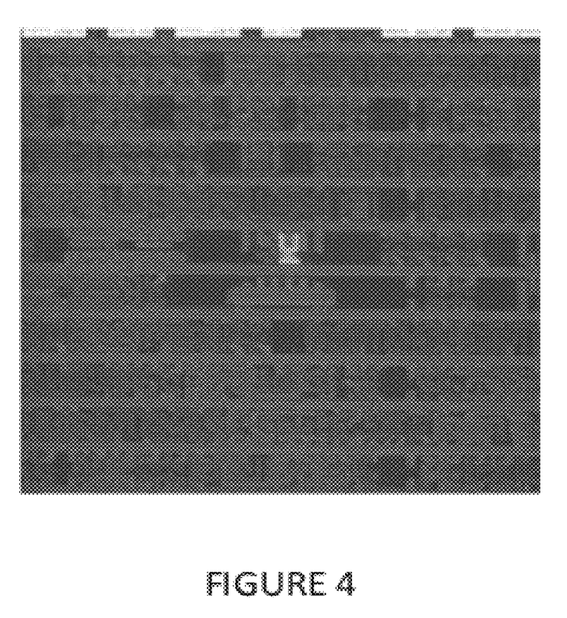
FIG. 4 is an image of a feature in high contrast using FIB.
Figure 5:
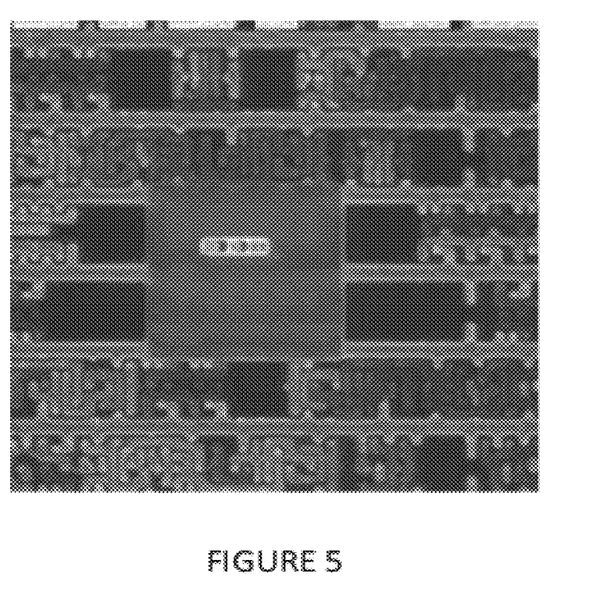
FIG. 5 is an image of the feature in FIG. 4 with a dielectric patch deposited.
Figure 6:
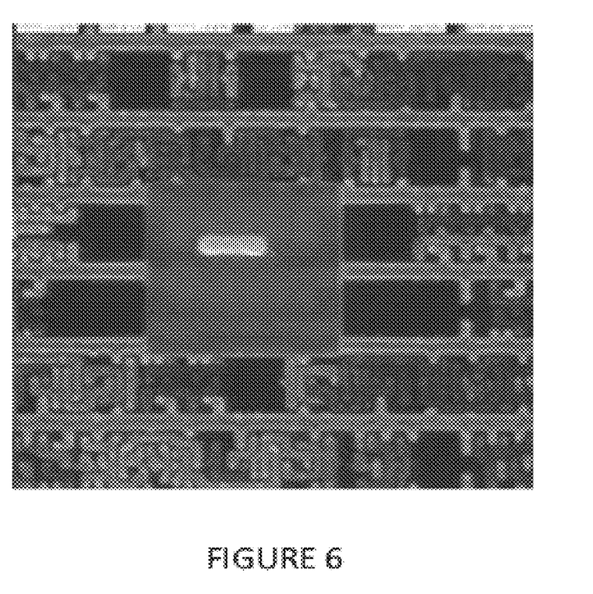
FIG. 6 is an image of the feature in FIG. 4 with the nodes of the known feature and of the unknown feature being shorted.

In FIG. 4, the known feature (a buffer) is biased and the FIB derived image shows the feature in high contrast relative to the other features on the IC. In FIG. 5, a dielectric patch is deposited on the known feature and the nodes of the known feature and an unknown feature (i.e. a non-biased feature) are exposed. In FIG. 6, the nodes of the known feature and of the unknown feature are shorted by depositing conductor material between the two nodes. Once shorted, the two nodes are thus coupled and applying a bias to the shorted nodes has the effect of applying a bias to whatever nodes, features, or components are coupled to the unknown feature. When a focused ion beam is thus applied to the IC while the bias is being applied, these nodes, features, or components coupled to the unknown feature will also appear in high (or higher) contrast when compared to the unbiased parts or areas of the IC.

Figure 7:
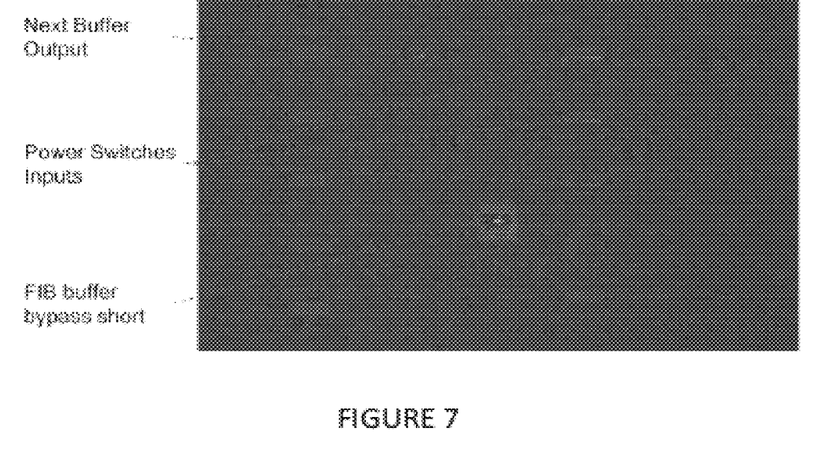
FIG. 7 is an image of the integrated circuit of FIG. 6 showing the different parts of the IC being in high contrast due to the bias being applied to the known feature.

Referring to FIG. 7, the shorted area (i.e. the area to which a bias has been applied) is illustrated in the lower middle part of the image. The features of the IC which are coupled to the unknown feature appear in higher contrast than the rest of the IC. As can be seen in FIG. 7, these features include inputs to the power switches as well as an output for the next buffer.

It should be noted that the example given in FIGS. 3A-7 should not be taken as being limiting to the present invention. Any feature, node, or component on an integrated circuit or microchip can be used as a first or initial component or node. This first component can then be shorted or coupled with a second component by any appropriate means prior to applying a bias and a focused ion beam to the integrated circuit. While the example given uses FIB to deposit and remove dielectric as well as metal interconnect, other techniques may be used. Also, while the example uses a gallium ion source for the focused ion beam, other ion sources, such as elemental gold, iridium, xenon, neon, as well any other suitable ion sources, may be used.

It should also be noted that, for best results, the first and second nodes or components which are to be coupled to each other are preferably not coupled to one another by way of the integrated circuit prior to being coupled to one another for biasing and imaging purposes.

In one implementation, to work one aspect of the invention, an integrated circuit chip or die is first prepared using standard known back-side sample preparation methods. This involves mounting the die to an insulating carrier face-down, then removing the die bulk silicon using wet or dry etching until the gate level components are exposed. The die can be further processed from the back using standard techniques to expose the specific layer of interest. One approach would be to expose the Metal 1 level. Once the level or component of interest has been exposed, a signal path is extended from an external source to the node, component, or feature of interest. A bias voltage is applied to the signal node or feature, typically using an external power supply.

After applying the bias voltage, the sample is then placed inside a focused ion beam chamber. The chamber is then pumped with a vacuum pump, and the sample is exposed to a FIB beam. By varying the beam conditions, the imaging detector conditions, and the external bias voltage, the signal node can be made to show up with very high contrast compared to the rest of the circuitry in the Secondary Electron (SE) imaging detector image. The node or feature of interest can be made to appear illuminated while the rest of the circuitry is dark.

Once the feature of interest has been biased and been made to appear in high contrast, the high contrast area can be extended. Using the ability of the focused ion beam technique to deposit insulating material and conducting material very precisely, the signal path is extended to a new section or feature of circuitry. In the case of a single transistor, the original biasing signal might be applied to one node of a transistor (e.g. a gate, source or drain contact) and, using focused ion beam deposition techniques, the biasing signal can be extended to another node of the transistor (e.g. gate, source or drain contact). Once the bias signal has been extended to the new feature, any other nodes connected to that node will appear illuminated in the SE image.

It should be noted that, while the signal path may extend invisibly through many metal layers (more than 10 on a modern IC), wherever it is connected to another metal 1 area will be instantly visible in the SE image.

Once the new connected node has been revealed, the procedure can be repeated and the next node can thus be illuminated. By continuing to traverse the circuit and form these connections, the circuit can be followed across the IC die. As can be imagined, for circuits involving a number of transistors, this process simply involves the deposition of conductor to short the source contact to the drain contact as well as the application of a bias voltage prior to applying the focused ion beam to the sample.

It should be noted that one aspect of the invention may take the form of simply applying an external bias to a component or node prior to applying a focused ion beam to the integrated circuit. After applying the focused ion beam, an image is taken using an electron detector. The features or components on the integrated circuit which are coupled to the component or node to which the bias was applied will show up in high contrast on the resulting image. The method can be used to identify nodes or components interconnected through a common path on the integrated circuit.

The technique outlined above can be applied to gate level circuitry, contact level circuitry, or any desired metal level (such as Metal 1).

It should be noted that the images obtained using the above outlined process may be further processed to glean further information from the images. As an example, image enhancement techniques may be applied to digital versions of the images derived from the above process to further clarify components, nodes, and features on the IC.

It should further be noted that the images gathered in multiple iterations of the process may be used to determine which features have been highlighted by the application of a bias to relevant part or parts of the integrated circuit. As an example, an image for iteration A (prior to applying a bias to a shorted part of the IC) may be compared to the image for iteration A+1 (subsequent to the application of the bias) to see which parts of the IC have been highlighted. Image subtraction, image manipulation, as well as image addition techniques may be used to automate the process by which the highlighted or highly contrasted parts of the image are determined.

Regarding the conditions and settings for the focused ion beam, various parameters may be adjusted and/or set for optimum resulting image quality. These parameters include voltage, current, dwell time, as well as other parameters. Such parameters and their effects and settings are well known to those versed in the art of focused ion beam techniques. For the electron detector, parameters which may be adjusted to obtain a suitable image quality include, among others, brightness, contrast, and line averaging.

The bias applied to the features of interest may range from +24V+ to −24V. The bias may depend on the focused ion beam conditions as well as the characteristics of the IC being imaged. As examples, the characteristics of the IC may include pattern density, conductor line width/resistance, dielectric quality and conductor quality. Preferably, bias current will be limited to prevent arcing between conductors. The bias current is thus preferably in the microampere range.

Figure 8:
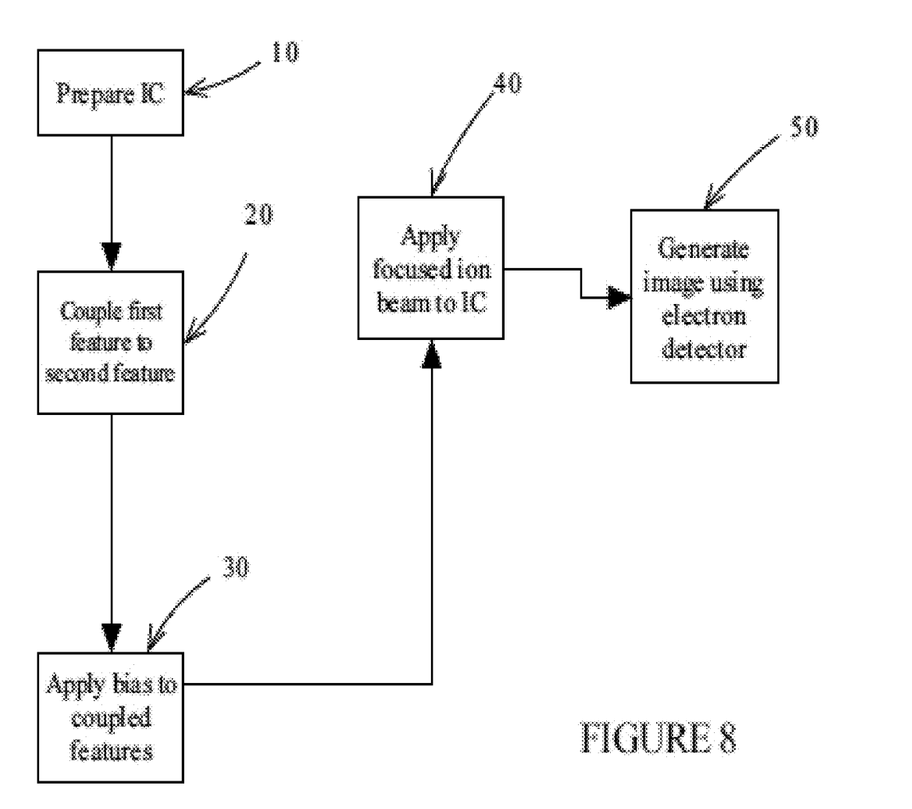
FIG. 8 is a flowchart detailing the steps in a method according to one aspect of the invention.

One aspect of the invention may be seen as a process detailed by the flowchart in FIG. 8. The process begins at step 10, that of preparing the IC. As noted above, this step may involve exposing the components in the IC to the gate level. Step 20 is that of coupling one feature or node to another. This may be done using different techniques including FIB dielectric deposition. Once a known feature has been coupled to an unknown feature (i.e. a feature whose interconnections are not known), a bias can then be applied to the coupled features (step 30). A focused ion beam can now be applied to the IC (step 40). An electron detector can then be used to generate an image of the IC (step 50). The IC features attached to the biased nodes or features will thus be in high contrast in the resulting image.

A person understanding this invention may now conceive of alternative structures and embodiments or variations of the above all of which are intended to fall within the scope of the invention as defined in the claims that follow.

We claim:

1. A method for identifying a signal path associated with a component of interest in an integrated circuit, the method comprising:

identifying a component of interest exposed on an integrated circuit device;

applying an external bias voltage to said component of interest;

capturing an image of at least a portion of said integrated circuit using a focused ion beam and an electron detector;

determining from said image a signal path associated with said component of interest shown in high contrast in said image due to electrical connectivity with said component of interest;

extending the signal path from a connected portion of said signal path, said connected portion in electrical connectivity with said component of interest, by coupling said connected portion to one or more unconnected portions of circuitry that are not in electrical connectivity with said component of interest; and repeating said capturing and said determining.

2. The method of claim 1, wherein the connected and unconnected portions are nodes on a given feature on said signal path.

3. The method of claim 2, wherein the nodes of the given feature are a source and corresponding drain of the given feature.

4. The method of claim 2, wherein the given feature comprises a gate.

5. The method of claim 2, wherein the given feature comprises a transistor.

6. The method of claim 2, wherein the given feature comprises a switch.

7. The method of claim 2, wherein the given feature comprises a power switch.

8. The method of claim 2, wherein the given feature comprises a buffer.

9. The method of claim 1, wherein said extending and said repeating of said capturing and determining are iteratively repeated one or more times.

10. The method of claim 9, wherein said iterative repeating is carried out until a signal path reaches one or more additional components of interest.

11. The method of claim 1, wherein the parts of the integrated circuit to be imaged in the step of capturing is determined automatically from images from a prior captured image.

12. A system for identifying a signal path associated with a component of interest in an integrated circuit, the system comprising:

an ion beam chamber for receiving a circuit device, said ion beam chamber comprising a focused ion beam emitter configured to direct a focused ion beam towards said circuit device, and an electron detector for measuring an intensity of electrons resulting from an interaction of said focused ion beam and said circuit device, and a bias voltage connector for selectively applying an external voltage to the circuit device;

the electron detector configured to generate image data of at least a portion of said circuit device while the focused ion beam is directed toward said device and the external voltage has been applied to a component of interest on said circuit device, said image data defining a signal path on said circuit device associated with said component of interest, said signal path having high contrast relative to other parts of said circuit device in said image data due to electrical connectivity with said component of interest;

wherein the signal path is extended one or more times from a connected portion of said signal path to an unconnected portion of circuitry by coupling said connected portion to said unconnected portion and repeating said image data generation.

13. The system of claim 12, wherein the connected and unconnected portions are nodes on a given feature on said signal path.

14. The system of claim 13, wherein the nodes of the given feature are a source and corresponding drain of the given feature.

15. The system of claim 13, wherein the given feature comprises a gate.

16. The system of claim 13, wherein the given feature comprises a transistor.

17. The system of claim 13, wherein the given feature comprises a switch.

18. The system of claim 13, wherein the given feature comprises a power switch.

19. The system of claim 13, wherein the given feature comprises a buffer.

* * * * *